United States Patent [19]

Fraini et al.

[11] Patent Number: 5,340,937
[45] Date of Patent: Aug. 23, 1994

[54] AVOIDING SULFONIC PHENOLS IN PRODUCTION OF PHENOLS

[76] Inventors: Edward A. Fraini, 117 Flag Dr. East, Lake Jackson, Tex. 77566; George W. Tepera, Rte. 1, Box 552, Sweeny, Tex. 77480; Malcolm W. McClure, Rte. 2, Box 1915-1; County Rd. 36, Angleton, Tex. 77515

[21] Appl. No.: 2,288

[22] Filed: Jan. 8, 1993

[51] Int. Cl.$^5$ ............................................. C07C 39/00
[52] U.S. Cl. .................................... 569/716; 568/717; 568/718; 568/720; 568/749
[58] Field of Search ............... 568/716, 749, 717, 718, 568/720

[56] References Cited

U.S. PATENT DOCUMENTS

| | | | |
|---|---|---|---|
| 2,768,977 | 10/1956 | Auvil et al. | 568/716 |
| 2,928,882 | 2/1960 | Hall | 568/716 |
| 4,661,637 | 4/1987 | Scouten | 568/716 |

*Primary Examiner*—Werren B. Lone

[57] ABSTRACT

This invention includes an improved process of converting a phenate to a phenol using acid in which a two phase system having an aqueous phase containing phenate and an organic, phenol-containing, phase are present, the improvement comprising adding the acid to enter the aqueous phase while avoiding contact of the acid and phenol phase. Preferably, with sufficient mixing to substantially surround the organic phase with the aqueous phase. The addition is preferably accomplished by mixing the two phases sufficiently to disperse a small organic (phenol) phase in a (bulk) aqueous phase. Such a process conveniently comprises the steps of: (a) mixing a system containing an organic phenol-containing phase and an aqueous phase sufficiently to substantially surround regions of organic phase with aqueous phase; and (b) adding acid to the aqueous phase; and, optionally, (c) maintaining sufficient mixing to prevent contact of concentrated acid with the organic or phenol phase.

19 Claims, 2 Drawing Sheets

AVOIDING SULFONIC PHENOLS IN PRODUCTION OF PHENOLS

This invention relates to recovery of a phenol from an aqueous phenate solution.

In the process of a number of chemical reactions, phenates are formed. Such processes include recovery of phenols from waste water streams, treatment of process waters, and pre-treatment of starting material, e.g., cumene, streams to remove phenol from feed stocks. Acids advantageously sulfuric acid, are often used to convert the phenates to the corresponding phenols.

Acids frequently react with the phenols to form undesirable by products. Avoiding formation of such by products would be desirable.

SUMMARY OF THE INVENTION

This invention includes an improved process of converting a phenate to a phenol using acid in which a two phase system having an aqueous phase containing phenate and an organic, phenol-containing, phase are present, the improvement comprising adding the acid to enter the aqueous phase while avoiding contact of the acid and phenol phase. Such addition is preferably accomplished by mixing the two phases sufficiently to disperse a small organic (phenol) phase in a (bulk) aqueous phase.

Such a process comprises the steps of
(a) mixing a system containing an organic phenol-containing phase and an aqueous phase sufficiently to substantially surround regions of organic phase with aqueous phase;
(b) adding acid to the aqueous phase; and, optionally,
(c) maintaining sufficient mixing to prevent contact of concentrated acid with the organic or phenol phase.

DETAILED DESCRIPTION OF THE INVENTION

Figure 1:
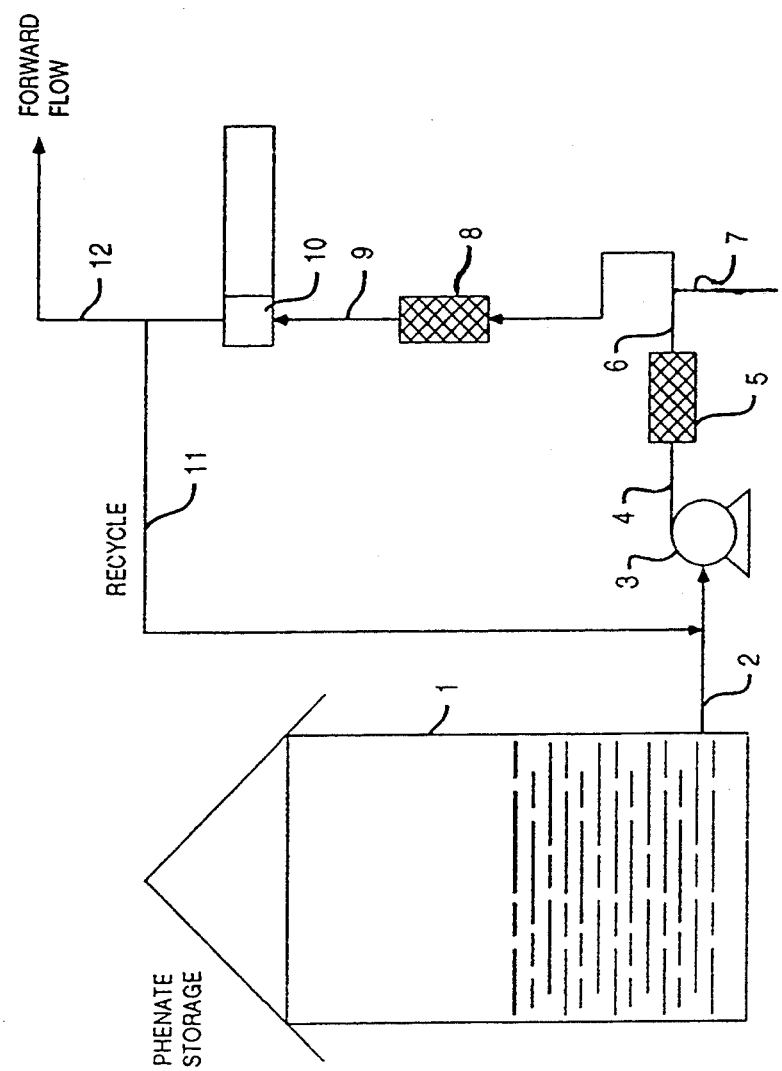
FIG. 1 illustrates an embodiment of the process of the invention.

The invention is applicable to any phenol which is sufficiently acidic to form water soluble phenates. Such phenols include phenols having from one to about 3 aromatic rings and being unsubstituted or having inert substitutents, that is substitutents which do not undesirably render the phenols insoluble. Such substitutents include, for instance alkyl groups of 1 to about 4 carbons, ketone groups, hydroxyl groups and the like Such phenols include, for instance, cumyl phenols, butyl phenols, creosols, and p-hydroquinone.

The process of the invention is applicable to any water soluble phenate, that is salt of a phenolic compound. The phenates are preferably alkali metal salts because of their solubility in water.

In the process of the invention, the phenate is at least partially dissolved in water (either deliberately or as a result of preceding steps or conditions) and acid is added to the resulting solution. When the acid reacts with the phenate, the phenol and the salt of the acid are formed. This part of the process is within the skill in the art. As the phenol is formed it separates into an organic phase.

Any acid with a lower pKa than the phenolic compound to be recovered is suitably used. Such acids include oxalic, acetic, formic, hydrochloric, phosphoric, sulfuric acids and mixtures thereof. Preferably the acid is sulfuric or phosphoric, most preferably sulfuric acid because of compatibility with commonly used materials of construction, that is, they are less corrosive to such materials as Austenitic steels such as 304, 304l, 316 and 316l.

Aqueous phases having some phenol phase (usually in relatively small proportions such as ratios of phenol phase to aqueous phase of from about one to three to about one to ten by weight frequently occur when some acid has already been added to an aqueous phase, when there is recycle of the aqueous phase from which a phenol has been at least partially phase separated or when various streams are combined from phenol producing processes such as cumene oxidation process such that the pH of the aqueous stream has been lowered to a point that at least a portion of a phenolic compound has been released from a corresponding salt form and the limit of solubility in the aqueous phase has been exceeded. Practice of the invention is particularly applicable to these situations.

In the practice of the invention, contact between the phenol and concentrated acid is avoided to avoid formation of such by-products as phenol sulfonic acids when sulfuric acid is used. Such by-products are to be avoided because they reduce the yield of phenol, are water soluble and, therefore, difficult to remove from a waste stream and because they can act as emulsifiers which further complicate product recovery and waste separation. In the practice of the invention, total sulfonated phenolic compounds are advantageously less than about 3, more preferably less than about 2 most preferably less than about 1, weight percent of total aqueous and organic phases. More advantageously, the weight ratio of sulfonated phenolic compounds to total phenolic compounds produced is less than about 0.6, more preferably less than about 0.3, more preferably less than about 0.15. Most advantageously, total phenolics (free phenolic compounds excluding phenate salts) in the aqueous phase are less than about 1000 ppm, preferably less than about 500 ppm, more preferably less than about 100 ppm, most preferably less than about 60 ppm.

Contact between the phenol phase and concentrated acid can be avoided in one or more of several different ways, For instance, acid can be added directly to the aqueous phase when the phases are separated, for example by an entry port into that phase or by means of a tube into that phase, said tube optionally going through a organic (phenol-containing) phase. A tube or other port for acid addition advantageously extends through and beyond the wall of a pipe, tube, vessel or other container of aqueous and organic phases into a region of predominately aqueous phase. Advantageously pooling of the acid which would result in a higher probability of contact with the phenol phase is avoided such as by adding acid through a tube into the aqueous phase or mixed phases such that the acid can rapidly disperse into the aqueous phase rather than adding it through a port having dead space, or otherwise by avoiding dead space where acid could accumulate.

In a commercial plant, it has been found particularly advantageous to mix the organic and aqueous phases sufficiently that the aqueous phase substantially surrounds the organic phase (that is to disperse the organic phase in the aqueous phase) at the time acid is added. By substantially surrounds it is meant that at least a majority of regions of organic phase are surrounded by aqueous phase.

Figure 2:
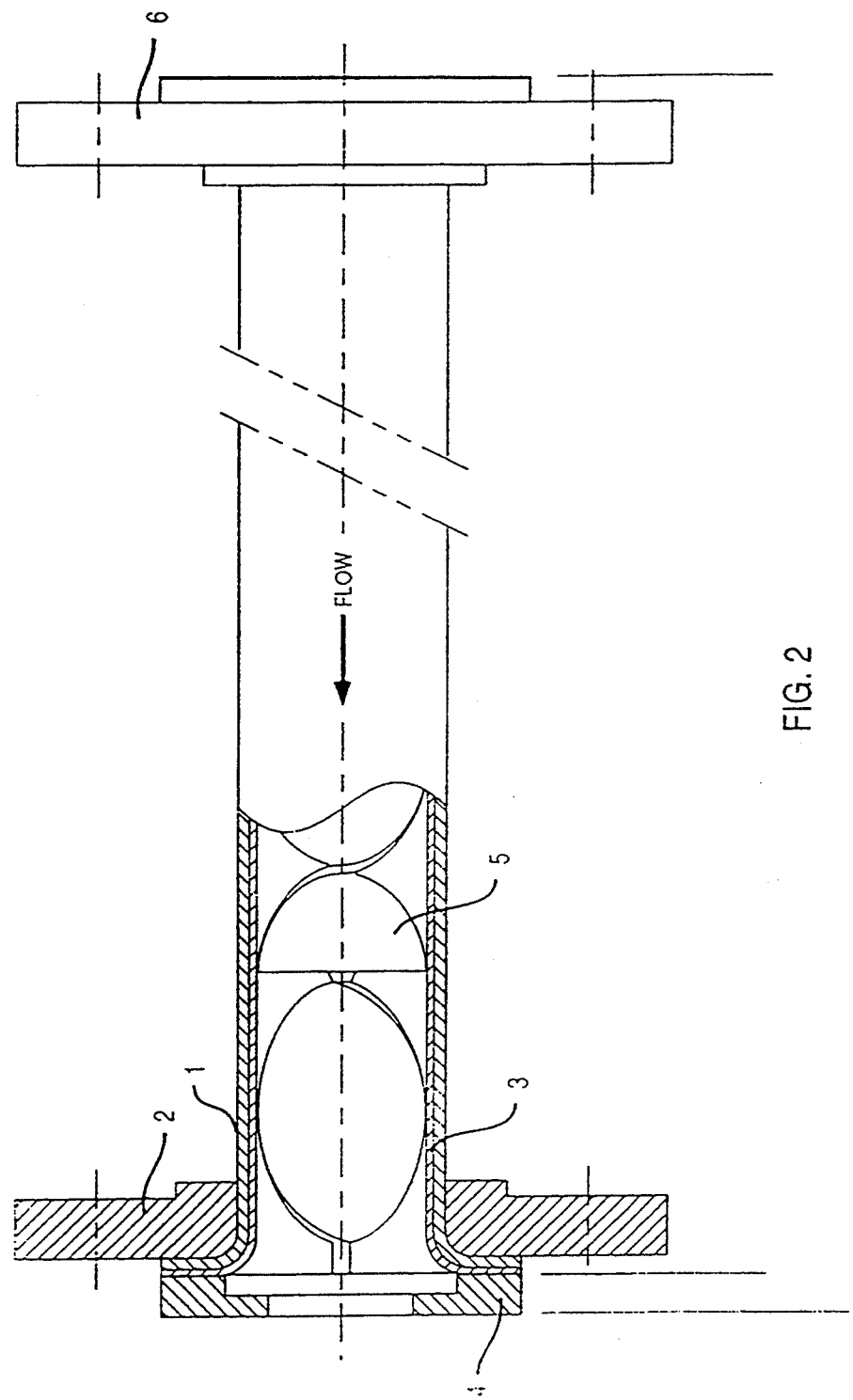
FIG. 2 illustrates a mixer useful in the practice of the invention.

Any mixing apparatus which accomplishes such a degree of mixing is suitably used in the practice of the invention. Such mixers include static mixers, stirred pot mixers, mixing orifices, values, and the like. Preferably, mixers which have stationary mixing elements are used. Such a mixer advantageously has, for instance, a helical or twisted member such as is illustrated in FIG. 2, and sufficient openings for flow. It is important that the mixer and any tubes entering the aqueous phase be resistant to deterioration caused by the acidic and phenolic environment. While glass or less resistant materials are suitable for many uses including laboratory use, materials such as polytetrafluoroethylene are particularly preferred in such corrosive environments as commercial phenol production.

In FIG. 2, a cylindrical housing member (1), for instance a pipe, is connected to a system through which phenate-containing liquid flows via a first flange (2) and a second flange (6). The housing member has a lining (3) which is preferably polytetrafluoroethylene. A gasket (4) is used between the first flange and the remainder of the system. The housing member contains a stationary mixing member (5) which is shaped to achieve mixing in a liquid flowing through the housing member.

To achieve substantial surrounding of organic phase regions by aqueous regions at the time to acid is introduced, the acid is preferably introduced after the mixing but before the phases have time to coalesce. Suitable times between mixing and acid addition are, thus, a function of equipment used because the degree of mixing and time until the organic phase coalesces will differ with different mixers and different equipment geometry which may facilitate or retard coalescing of the organic phase. In general, however, the system the phenol phase is advantageously very finely dispersed. If flow is turbulent, the addition point can be at great lengths from the mixer such as about 100 pipe diameters. If the flow is in either the transition or the laminar phase, the dispersed phase will immediately begin to coalesce as it exits the mixer. In the latter instance, an acid addition point is preferably one to five pipe diameters from the mixer outlet. Most preferably, with operation in the transition phase or just slightly above it, the location of acid addition is less than five pipe diameters from the mixer. The pipe diameter is that of the pipe (or other apparatus) through which the phases flow after mixing.

Mixing is advantageously maintained or again introduced after addition of the acid to achieve contact between the acid and phenate solution. For instance, a mixer is optionally used after the point of acid addition. Such a mixer is advantageously of any of the types used before the point of acid addition.

Conditions of temperature and pressure are not critical for this process. It can occur at any pressure under which liquid phases are maintained, conveniently at the pressures commonly found in a range of from about 0 to about 6 atmospheres gauge (0 to $6.02 \times 10^5$ kPa) most conveniently at atmospheric pressure ($1.013 \times 10^5$ kPa). Temperatures are conveniently any which liquid phases are maintained, conveniently at the temperatures commonly found in processes in which a phenol is produced, e.g. from about 20° C. to 150° C., most conveniently from about 25° C. to about 100° C.

FIG. 1 illustrates an apparatus useful in the practice of the invention; the apparatus includes a tank (1) containing aqueous phenate solution, a first pipe (2) connected at its first end near the bottom of the tank, a pump (3) connected to the first pipe distal from its connection to the tank (for entry of the phenate solution into the pump) and a second pipe (4), a first static mixer (5), connected to the second pipe distal from the pump, through which the phenate enters the mixer and a third pipe (6) through which it exits; a injector tube (7) entering the third pipe; said injector tube entering the wall of the third pipe and having an outlet approximately at the center of the third pipe and an inlet outside the third pipe which injector tube is preferably made of or lined with an acid resistant substance such as polytetrafluoroethylene; a second static mixer (8) connected to the third pipe at an end distal from the exit of the first static mixer and connected to a fourth pipe (9), said fourth pipe connected distal from the second mixer to a water cooler (10) to remove heat of neutralization (heat produced by reacting the phenate with an acid), said water cooler being connected to a fifth pipe (12) for exit of the phenol and phenate solution (e.g. to the remainder of a process or to further processing, and a recycle pipe (11) forming a tee with the fifth pipe for exit of a portion of the aqueous phenate/phenol liquid mixture from the fifth pipe and returning to the first pipe between the tank and the pump.

The stream leaving the second mixer is preferably two phase, the bulk phase is an aqueous stream containing salts formed by the reaction of acid and the residual unreacted sodium phenates. The second phase is essentially pure phenol, produced by the reaction, because the solubility limit of the water layer is exceeded. Acid is added through the injector tube. A recycle stream in the recycle pipe contains the two phases (a larger aqueous phase containing dissolved sodium phenate and a smaller organic (phenol) phase). The first static mixer disperses the phenol phase.

The following examples are offered to illustrate and not to limit the invention. Examples of the invention are designated numerically, while comparative examples are designated alphabetically. All ratios, percentages, and parts are by weight unless designated otherwise.

EXAMPLE 1 AND COMPARATIVE SAMPLE A

Small Scale Evidence of Value of Addition of Acid to Aqueous Phase

A small laboratory reactor is prepared from a test tube by clamping the test tube in a beaker above a magnetic stirrer, placing a magnetic stir bar in the tube, charging the tube with 50 grams of an aqueous sodium phenate solution (18 weight percent), corking the tube with a cork having a pH probe leading to a commercially available pH meter and a tube (port) for acid injection therethrough. Both the probe and tube reach into the solution with the bottom of the tube below that of the pH probe. The beaker contains cold water (30° C.) to cool the reaction. Concentrated sulfuric acid (99 percent by weight) is added through the addition port until a pH of 7.0 is observed. A second layer, essentially pure phenol, is formed. Acid addition is made only to the lower aqueous phase by injection into the port having its exit well into the aqueous layer.

In a Comparative Sample A, the same apparatus and procedures are used as for Example 1 except that once the second layer forms the addition port exit is raised so that the concentrated sulfuric acid is added to the upper, phenol, phase. Table 1 shows the large difference in the amounts of the undesirable sulfated phenolic compounds produced.

The analysis represented in Table 1 is done by liquid chromatography using a reverse phase column commercially available from E. I. Dupont de Nemours and Company under the trade designation ZORBAX ™.

TABLE 1

| Analysis of Aqueous Phase | | |
|---|---|---|
| | Example 1 | Comparative Sample A |
| phenol | 2.5 percent by weight | 2.5 percent by weight |
| para-hydroxybenzene sulfonate | 800 ppm | 1.49 percent by weight |
| ortho-hydroxybenzene sulfonate | 1350 ppm | 3.07 percent by weight |

This example shows that a direct contact of concentrated $H_2SO_4$ with phenol results in the formation of sulfonated phenols, an undesirable by product which is greatly reduced by practice of the invention as represented by Example 1.

EXAMPLE 2 AND COMPARATIVE SAMPLE B

Larger Scale Example of Use of Stirring to Avoid Contact of Acid and Phenol

An apparatus includes a tank from which aqueous phenate (19.2 weight percent) weight percent) is pumped, a first pipe (7.62 cm diameter) connected at its first end near the bottom of the tank, a pump connected to the first pipe distal from its connection to the tank (for entry of the phenate solution into the pump) and a second pipe (same diameter, for exit), a first static mixer connected to the second pipe distal from the pump through which the phenate enters the mixer and a third pipe (same diameter) through which it exits; a smaller (1.27 cm diameter) polytetrafluoroethylene injector tube entering the third pipe, said injector tube entering the wall of the third pipe and having an outlet approximately at the center of the third pipe and an inlet outside the third pipe; a second static mixer connected to the third pipe at an end distal from the exit of the first static mixer and connected to a fourth pipe (same diameter), said fourth pipe connected distal from the second mixer to a water cooler sufficient to remove the heat of neutralization (heat produced by reacting the phenate with an acid), said water cooler being connected to a fifth pipe (same diameter) for exit of the phenate solution, and a recycle pipe forming a tee with the fifth pipe for exit of a portion of the aqueous phenols/phenol liquid mixture from the fifth pipe and returning to the first pipe between the tank and the pump.

The stream leaving the second mixer is two phase, the bulk phase is an aqueous stream containing salts formed by the reaction of sulfuric acid and the residual unreacted sodium phenates. The second phase is essentially pure phenol, produced by the reaction, because the solubility limit of the water layer is exceeded. The total flow rate of this stream is 100 gallons per minute (378.5 liters/minute). The stream is passed through a heat exchanger to remove the heat of reaction. By controlling forward flow with a flow control valve only 25 gallons (94.6 liters) per minute of the mixed stream is fed forward for recovery of the phenol. The balance, 75 gallons (283.9 liters) per minute comprising fractions of both phases is recycled back to the pump suction to provide dilution to lower the fresh feed phenate concentration so that the heat of reaction is moderated. It is this mixed stream recycle that introduces the phase separated phenol to a point up stream of the acid addition point.

The pump and piping before the acid addition point are stainless steel. The addition tube is polytetrafluoroethylene (PTFE). PTFE is advantageous because corrosion is a function of temperature, and the heat of reaction is localized to the addition point. The pipe segment into which the addition is made is lined with PTFE.

The phenate solution is pumped at a rate of 100 gallons per minute (378.5 liters/minute) from the tank through the first and second pipes and through the first mixer into the third pipe into which sulfuric acid is added at a rate sufficient to lower the pH to 9.5 (about 800 lbs/hr) (360 kg/hr) through the injector tube. The total stream cooled from about 100° C. to about 30° C. by the water cooler. A portion, 75 percent, is recycled to the pump suction to provide dilution of the concentrated phenate solution. This recycle stream contains the two phases (a larger aqueous phase containing dissolved sodium phenate and a smaller organic (phenol) phase). The first static mixer disperses the phenol phase. The injector tube is used to inject the acid into the aqueous phase.

Table 2 shows the difference between the amounts of total phenolics (phenols, sulfonic phenols and other phenolic by-products) in the practice of Example 2 compared with Comparative Sample B in which the process and apparatus of Example 2 are used without the first static mixer and with a pipe tee as an acid port in place of the injector tube; the pipe tee connects with the third pipe but does not go into it.

The analysis represented in Table 2 is done by liquid chromatography using a reverse phase column commercially available from Waters Associates under the trade designation NOVA-PAK ™ C18. Forward flow from the second mixer is processed through an extraction-unit operation where phenol is recovered by contacting the aqueous phase, which is saturated with phenol, with cumene extractant to remove the phenol and prepare it for discharge from the process. Samples are taken from the aqueous phase at the extractor outlet on different days of continuous operation at the indicated conditions. Other non-aqueous extractants such as aromatic or aliphatic hydrocarbons are optionally used in place of cumene.

TABLE 2

| Analysis of Aqueous Phase | |
|---|---|
| | total phenolics (phenol, sulfonated phenols, other phenolic by products) (in parts per million (ppm) by weight) |
| Example 2, first sample | 51 |
| Example 2, second sample | 49 |
| Example 2, third sample | 37 |
| Comparative Sample B, first sample | 2480 |
| Comparative Sample B, second sample | 3840 |
| Comparative Sample B, third sample | 1320 |
| Comparative Sample B, fourth sample | 3160 |
| Comparative Sample B, fifth sample | 2400 |

TABLE 2-continued

| Analysis of Aqueous Phase | |
|---|---|
| | total phenolics (phenol, sulfonated phenols, other phenolic by products) (in parts per million (ppm) by weight) |
| Comparative Sample B, sixth sample | 2640 |
| Comparative Sample B, seventh sample | 1960 |
| Comparative Sample B, eighth sample | 1560 |
| Comparative Sample B, ninth sample | 4080 |

The analysis in this example shows that a reduction of total phenolics can be achieved in the process of the invention (Example 2) as compared with a process having acid contact the phenol phase (Comparative Sample B). The reduction is a result of minimizing the amount of sulfonic phenolics in the Example.

We claim:

1. An improved process of converting a water soluble phenate to a corresponding phenol using an acid having a pKa lower than that of the phenol in which a two phase system having an aqueous phase containing both the phenol and the phenate and an organic, phenol-containing, phase are present, the improvement comprising adding the acid to enter the aqueous phase with mixing sufficient to substantially surround the organic phase with the aqueous phase.

2. The process of claim 1 wherein the two phases are mixed sufficiently to disperse an organic, hereinafter phenol, phase in a bulk aqueous phase.

3. The process of claim 1 wherein the acid is oxalic, acetic, formic, hydrochloric, phosphoric, sulfuric acid or a mixture thereof.

4. The process of claim 3 wherein the acid is phosphoric, sulfuric or a mixture thereof.

5. The process of claim 4 wherein the acid is sulfuric.

6. The process of claim 5 wherein the phenol is unsubstituted phenol.

7. The process of claim 5 wherein less sulfonated phenol is formed than is formed when the same quantity of the acid is added to the organic phase.

8. The process of claim 5 wherein less sulfonated phenol is formed than would be formed without mixing sufficient to substantially surround the organic phase with aqueous phase.

9. The process of claim 5 wherein the concentration of sulfonated phenols in the combined aqueous and organic phases is less than about 3 percent by weight.

10. The process of claim 5 wherein the weight ratio of sulfonated phenolic compounds to total phenolic compounds is less than about 0.6.

11. The process of claim 5 wherein the aqueous phase contains less than about 1000 ppm phenolic compounds.

12. The process of claim 1 wherein adding the acid to enter the aqueous phase is accomplished by adding acid through a port extending beyond the wall of a pipe or vessel containing the aqueous and organic phases into a region of predominately aqueous phase.

13. A process comprising the steps of:
    (a) mixing a system containing an organic phenol-containing phase wherein the phenol is sufficiently acidic to have a corresponding water soluble phenate and an aqueous phase sufficiently to substantially surround regions of organic phase with aqueous phase; and
    (b) adding an acid having a pKa lower than that of the phenol to the aqueous phase.

14. The process of claim 13 additionally having a step
    (c) maintaining sufficient mixing to prevent contact of concentrated acid with the organic or phenol phase.

15. The process of claim 13 wherein at least a portion of the aqueous phase is a recycle stream from production of a phenol.

16. The process of claim 13 wherein the production of a phenol is the production of unsubstituted phenol from cumene.

17. The process of claim 13 wherein the concentration of sulfonated phenols in the combined aqueous and organic phases is less than about 3 percent by weight.

18. The process of claim 13 wherein the weight ratio of sulfonated phenolic compounds to total phenolic compounds is less than about 0.6.

19. The process of claim 13 wherein the aqueous phase contains less than about 1000 ppm phenolic compounds.

* * * * *